(12) United States Patent
Boss

(10) Patent No.: US 9,486,382 B1
(45) Date of Patent: Nov. 8, 2016

(54) EXERCISE MACHINE

(71) Applicant: Dimitry Ralph Boss, Hillsdale, NJ (US)

(72) Inventor: Dimitry Ralph Boss, Hillsdale, NJ (US)

(*) Notice: Subject to any disclaimer, the term of this patent is extended or adjusted under 35 U.S.C. 154(b) by 0 days.

(21) Appl. No.: 14/664,840

(22) Filed: Mar. 21, 2015

Related U.S. Application Data

(60) Provisional application No. 61/968,520, filed on Mar. 21, 2014.

(51) Int. Cl.
| | |
|---|---|
| *A61H 1/00* | (2006.01) |
| *A61H 1/02* | (2006.01) |
| *A61B 5/01* | (2006.01) |
| *A61B 5/02* | (2006.01) |

(52) U.S. Cl.
CPC .............. *A61H 1/0218* (2013.01); *A61B 5/01* (2013.01); *A61B 5/02* (2013.01); *A61H 1/003* (2013.01); *A61H 2201/1284* (2013.01); *A61H 2201/5007* (2013.01)

(58) Field of Classification Search
CPC ............ A63B 23/0211; A63B 23/038; A63B 23/00185; A63B 23/4009–23/4015; A63B 22/14–22/18; A63B 2208/0285; A61H 1/0218–2001/0233; A61H 2203/0493
USPC ................. 482/144; 446/44, 46, 47
See application file for complete search history.

(56) References Cited

U.S. PATENT DOCUMENTS

| | | | |
|---|---|---|---|
| 2,054,402 A * | 9/1936 | Williams ............... | A61H 1/001 482/907 |
| 3,519,268 A | 7/1970 | McQueen | |
| 3,936,047 A | 2/1976 | Brandt et al. | |
| 4,113,250 A | 9/1978 | Davis | |
| 4,391,443 A | 7/1983 | Beecroft | |
| 4,746,116 A * | 5/1988 | Inada ..................... | A63B 19/04 482/145 |
| 5,094,249 A | 3/1992 | Marras et al. | |
| 5,695,438 A * | 12/1997 | Bjornsti ................. | A63B 19/04 482/144 |
| 5,941,807 A | 8/1999 | Cassidy et al. | |
| 2005/0187085 A1* | 8/2005 | Webb ................. | A63B 21/4037 482/140 |
| 2011/0306891 A1* | 12/2011 | Crompvoets ...... | A61B 5/02438 600/508 |
| 2012/0237911 A1* | 9/2012 | Watterson .......... | A63B 24/0087 434/247 |

* cited by examiner

*Primary Examiner* — Loan H Thanh
*Assistant Examiner* — Jennifer M Deichl
(74) *Attorney, Agent, or Firm* — Quickpatents, LLC; Kevin Prince

(57) ABSTRACT

An exercise device having a rigid base includes at least one frame fixed with and extending upwardly therefrom. An outer barrel is rotationally fixed with the upper end of each frame at a tilt mechanism. Both an outer barrel and an inner barrel are open from a top side to a bottom side thereof for accommodating the person therein. At least one inflatable cushion is fixed with an inner side of the inner barrel. An adjustable leg support mechanism projects downwardly from the inner barrel and is adapted to support the person's feet and legs. An electric control console controls motorized tilt and spin mechanisms to tilt the outer barrel with respect to vertical and spin the inner barrel with respect to the outer barrel. Preferably the control console further includes at least a processor, a computer-readable storage medium, a display, an input interface, and a network interface.

21 Claims, 15 Drawing Sheets

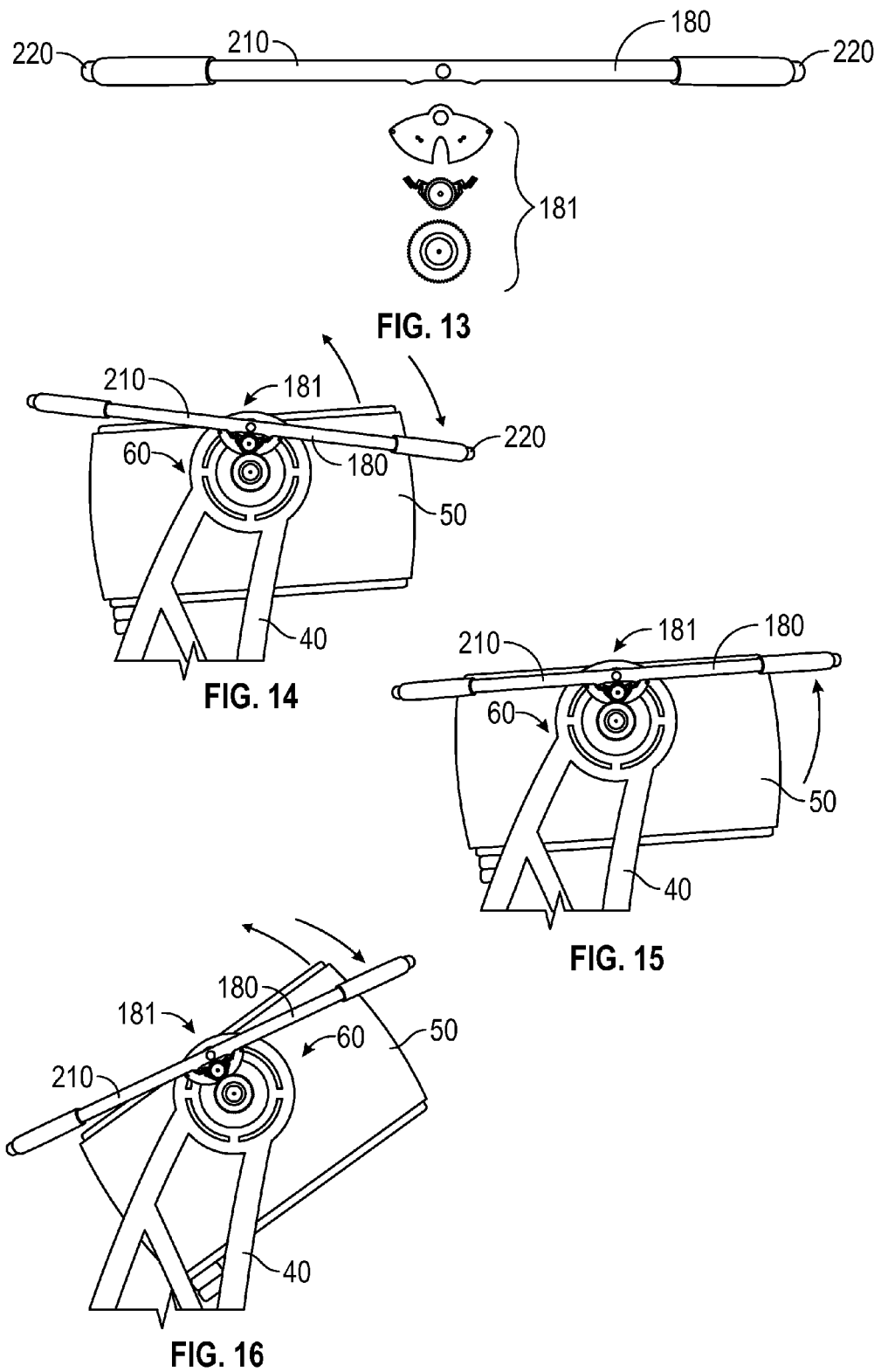

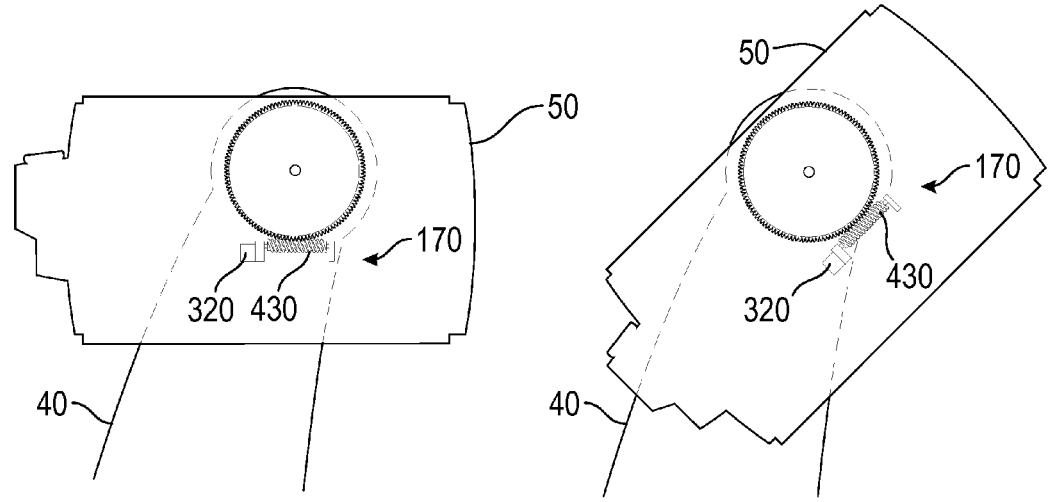
FIG. 17A  FIG. 17B
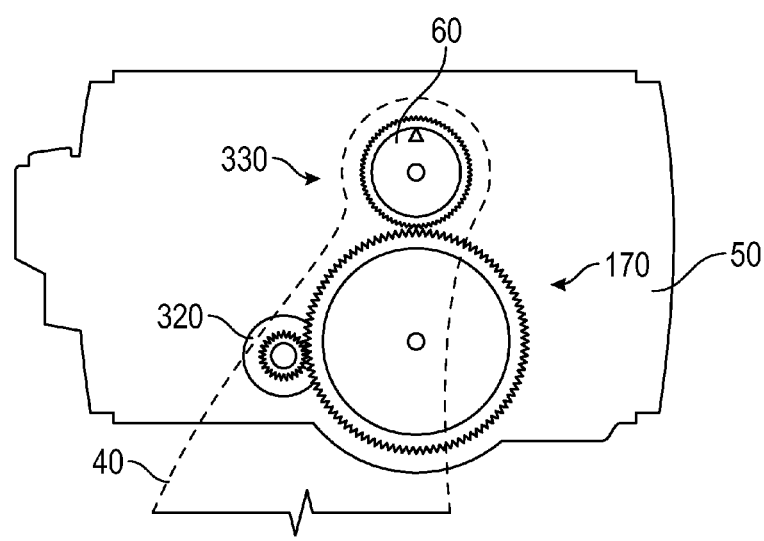
FIG. 18

EXERCISE MACHINE

CROSS-REFERENCE TO RELATED APPLICATIONS

This application claims the benefit of U.S. Provisional Patent Application 61/968,520, filed on Mar. 21, 2014, and incorporated herein by reference.

STATEMENT REGARDING FEDERALLY SPONSORED RESEARCH AND DEVELOPMENT

Not Applicable.

FIELD OF THE INVENTION

This invention relates to exercise machines, and more particularly to an exercise machine that allows exercising of a relatively large number of muscle groups in a relatively low amount of floor space.

DISCUSSION OF RELATED ART

A wide variety of exercise devices exist in the prior art to help people exercise various muscle groups, particularly the abdominal muscles. Many such prior art abdominal muscle exercising devices and machines, however, do not allow for fine adjustments to the angle of the person while using the device, resulting in uneven muscle strengthening. Further, such devices are muscle-group specific, only facilitating the exercising of one muscle group or type.

U.S. Pat. No. 2,054,402 to Williams on Sep. 15, 1936 teaches an exercising apparatus comprising an inner collar with cushioning means for supporting a person therein, the inner collar rotationally supported within an enclosing structure. The angle of the enclosing structure may be adjusted with respect to vertical, allowing the person to exercise while at various angles of tilt with respect to vertical and while at various rotational angles with respect to the enclosing structure. Such a device, however, relies on the strength of the user to manually adjust the various angles and rotations, and does little to facilitate the transition from one angular state to another. Further, such a device provides no emergency return-to-start provision in the event the user loses consciousness or suffers a medical emergency, for example. Further, such a device is not usable at tilt angles beyond 90-degrees as no provisions are made for holding the user's knees or ankles in place, which would result in the person slipping up out of the collar and falling out of the device.

U.S. Pat. No. 4,391,443 to Beecroft on Jul. 5, 1983 teaches a similar device that allows for tilting to angles of more than 90-degrees through the use of fixed boots for holding the person's feet in place. However, such a device does not provide for programmed control of a multi-position workout routine, or pre-programmed workout routines. Further, such a device does not provide for convenient motorized adjustment of the position of the user's feet with respect to the rotatable ring. Moreover, such a device has no opening in the ring, requiring that the aperture in the ring for receiving the exerciser is relatively large. As such, a device of this type requires a relatively large amount of space within an exercising gym. Further, as the user of such a device is often inverted or otherwise facing away from manual controls, the user sometimes has difficulty actuating switches with such a device for rotating or tilting the ring.

Therefore, there is a need for a device that allows for fully automated adjustment of tilt, rotation, and user height, and further provides for a programmed workout routine that advances from one device state to another in response to detection of the number of repetitions of an exercise performed or a preset duration. Such a needed device would provide for emergency shut-down and return of the device to a default position in the event of an emergency condition, and would detect various physiological states of the user for safety. Further, such a needed invention would require relatively little floor space, and would provide a compact inner barrel with inflatable cushions for securing the user therein and for detecting movement thereof. Such a needed device would not require the user to place his feet into rigid boots, but would rather more comfortably hold the user's feet with padded ankle bolsters. As the position of the user is sometimes inverted or backward with respect to any manual controls, such a needed invention would allow for the issuance of verbal commands. The present invention accomplishes these objectives.

SUMMARY OF THE INVENTION

The present device is an exercise device having a rigid base for supporting the exercise device on a floor surface. At least one frame is fixed with and extends upwardly from the base. An outer barrel is rotationally fixed with the upper end of each frame at a tilt mechanism. Both an outer barrel and an inner barrel have an outer side, an inner side, and are open from a top side to a bottom side thereof for accommodating the person therein. The barrels each have an opening therethrough for allowing ingress and egress of the person. At least one preferably inflatable cushion is fixed with the inner side of the inner barrel to support the person therewithin.

A leg support mechanism projects downwardly from the bottom side of the inner barrel and is adapted to support the person's feet and legs when the person is positioned within the inner barrel, and may further include a height-adjustable leg support frame fixed at a top end thereof with the inner barrel. The bottom end of the leg support frame terminates at a foot platform for supporting the person's feet thereon.

A pair of knee cuffs may be included, each knee cuff having an upper cuff and a lower cuff that are mutually pivotally attached at a back pivot thereof. The back pivot is lockable with a locking lever to prevent mutual rotation between each cuff. The locking lever may include a cam arrangement for binding the back pivot into a fixed and locked position when the locking lever is in a locked position. The leg support mechanism may further include, for each of the person's feet, at least one, and preferably two, padded foot bolster for aiding in supporting the person in positions where the outer barrel is tilted beyond 0-degrees in either direction.

In use, with the person positioned within the inner barrel and with his feet and legs supported by the leg support mechanism, the person may be tilted with respect to vertical and rotated with respect to the axis of the barrels in order to achieve different orientations in which to do exercises for exercising various muscles and muscle groups. Depending upon the selected tilt of the outer barrel and the selected rotation of the inner barrel, such muscle groups may include, for example, the torso, core, mid-section, rectus abdominals, transversus abdominis, lower back, internal oblique, external oblique, latissimus dorsi, serratus anterior, serratus posterior inferior, erector spinae, external intercoastal, gluteus maximus, and gluteus medius muscle groups.

In at least one embodiment, the exercise device further includes an electric control console, which is controllable by the person when positioned within the inner barrel. Each tilt mechanism, in such embodiments, includes a powered drive mechanism to tilt the outer barrel with respect to the frame in accordance to commands issued by the control console. Similarly, a powered spin mechanism may be further included and fixed between the inner and outer barrels, the spin mechanism including a powered drive mechanism to rotate the inner barrel with respect to the outer barrel in accordance to command issued by the control console. Preferably the control console further includes at least a processor, a computer-readable storage medium, a display, an input interface, and a network interface.

With such a computer-controlled embodiment, the air pressure within each inflatable cushion of the inner barrel may be read by an air pressure sensor and controlled by the control console, which can actuate an air pump to inflate the cushion, or actuate an electrically-actuated pneumatic valve to bleed-off air within the cushion into the environment. The cushions are deflated when the person wishes to exit the exercise device and when the barrels are in a default starting position, and inflated once the person is positioned within the inner barrel and indicates he is ready to start exercising. The person may also manually adjust the inflation pressure of the cushions for comfort and support as needed. In such an embodiment, with the air pump off and the pneumatic valve closed, the air pressure sensor can detect movement of the user by registering changing air pressure within the cushions related to pressure applied by the person to the cushions.

In such a computer-controlled embodiment, the control console is programmed to return the tilt and spin mechanisms to their default positions if an emergency condition is detected, such as detecting no activity or movement of the person for a predetermined period of time based on monitoring fluctuations in air pressure in the cushions or a separate motion sensor, an electrical ground fault, a power failure, actuation of an emergency stop button, deactivation of the control console by the person, or the like. In the case of a power failure or deactivation of the control console, the exercise device further preferably includes a rechargeable battery or capacitor of sufficient capacity to return the tilt and spin mechanisms to their default positions.

The network interface is preferably a wireless network interface, wherein the control console is programmed to receive commands from a remote electronic device of the person, such as a portable smart phone running an exercise application thereon. The control console, in such an embodiment, provides exercise statistics of the person to the remote electronic device via the wireless network interface. Workout routines may also be downloaded by the control console via the wireless network interface.

The processor is adapted to follow instructions stored in the computer-readable storage medium that enables the person to store his desired workout routine in the computer-readable storage medium. Pre-programmed workout routines may be included with the exercise device, or customized workout routines may be stored in the computer-readable storage medium through use of the input interface or the network interface and a remote device. Such a customized workout routine may be established by a health care professional or coach of the person, for example, through an internet-enabled remote device in communication with either the portable electronic device of the person or the exercise device directly. Such a workout routine includes one or more states that each include at least the position of the tilt mechanism and the spin mechanism, desired air pressure in each of the cushions, and a duration of time to perform exercises in that position and/or a number of reps that are to be performed while in that position. The application running on the portable electronic device may act as the control console in some embodiments Periodicity of air pressure variations within each cushion as detected by the pressure sensor allows the control console to count the number of repetitions of an exercise that the person has performed with the tilt and rotation mechanisms in a set position, and in this way the control console can determine based on a prescribed workout routine when to advance the tilt and rotation mechanisms a next state for the person to start a new exercise.

The control console may further include at least one physiological sensor such as a heart rate monitor, a body temperature sensor, a blood pressure sensor, or an oxygen absorption sensor. Such a physiological sensor may be attached to the person and include the wireless network interface, include a wired interface, or may be fixed with one of the cushions, for example. As such, physiological conditions and exercise statistics may be monitored and recorded by the control console and transmitted through the wireless network interface to the portable electronic device or another remote device, a social media or other website, or the like.

The present invention is an exercise device that suspends a user's torso and allows for fully automated adjustment of tilt, rotation, and user height, and further provides for a programmed workout routine that advances from one device state to another in response to detection of the number of repetitions performed by the user or a preset duration. The present device provides for emergency shut-down and return of the device to a default position in the event of an emergency condition, and is able to detect various physiological states of the user for safety. Further, the present invention requires relatively little floor space, and provides a compact inner barrel with inflatable cushions for securing the user therein and for detecting movement thereof. The present device does not require the user to place his feet into rigid boots, but rather more comfortably holds the user's feet with padded ankle bolsters. The present invention also allows for the convenient issuance of verbal commands. Other features and advantages of the present invention will become apparent from the following more detailed description, taken in conjunction with the accompanying drawings, which illustrate, by way of example, the principles of the invention.

DESCRIPTION OF THE DRAWINGS

FIG. 13 is an exploded view of one embodiment of the first and second control handles and a ratchet mechanism;

FIG. 14 is a side elevational diagram of the first control handle of the embodiment of FIG. 13 being pressed down or forward to tilt the outer barrel backward;

FIG. 15 is a side elevational diagram of the first control handle of FIG. 14 returning to a neutral position;

FIG. 16 is a side elevational diagram of the first control handle of FIG. 14 being once again pressed down or forward to tile the outer barrel backward even further;

FIG. 17A is a diagram of one embodiment of a powered drive mechanism for the tilt mechanism, the barrel at the default 0-degree tilt position;

FIG. 17B is a diagram of the embodiment of FIG. 17A, the barrel at an approximate 45-degree tilt position; and FIG. 18 is a diagram of yet another embodiment of a powered drive mechanism for the tilt mechanism.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
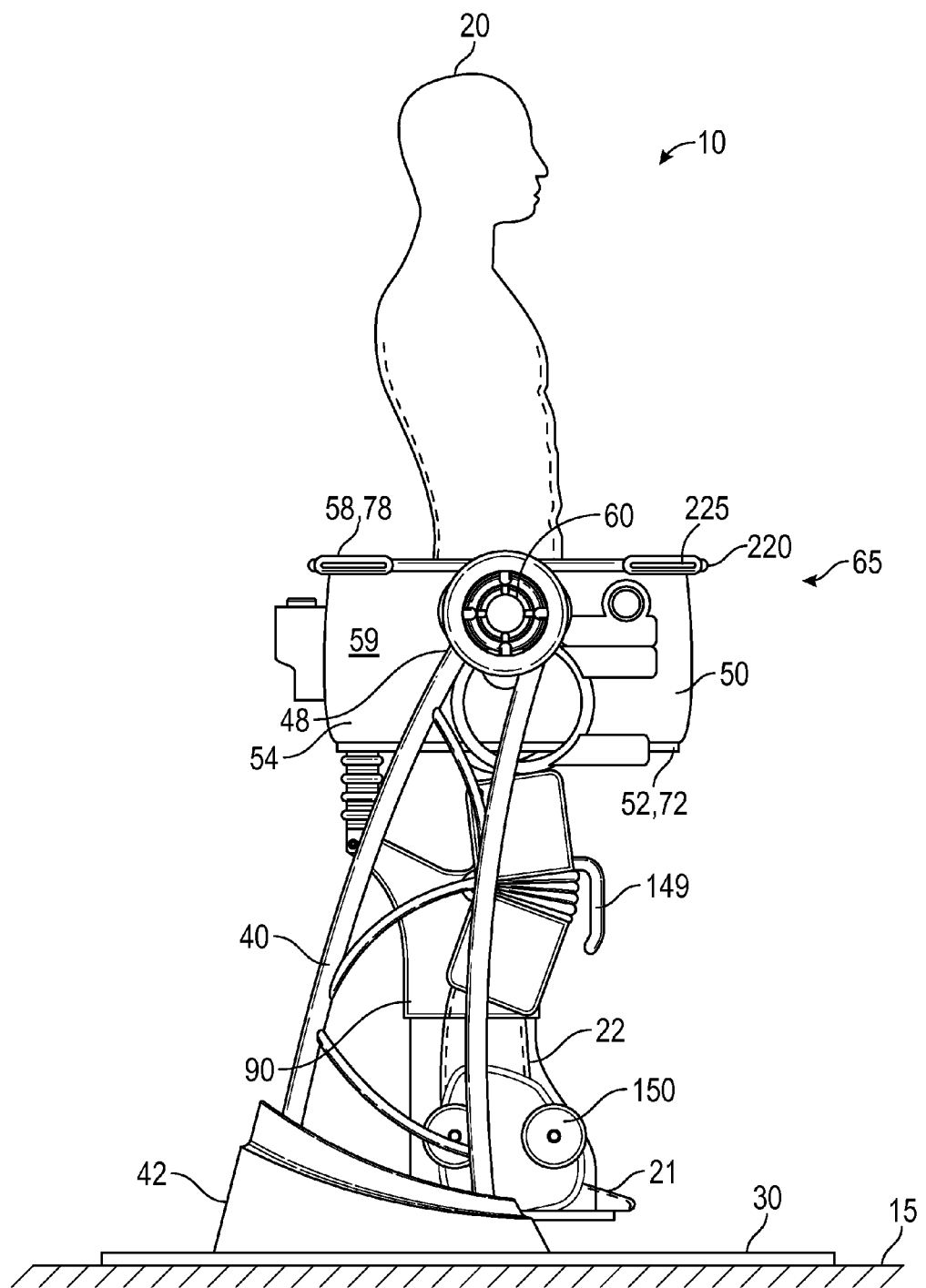
FIG. 1 is a side elevational view of the invention, showing an outer barrel and an inner barrel in a default position.
Figure 3:
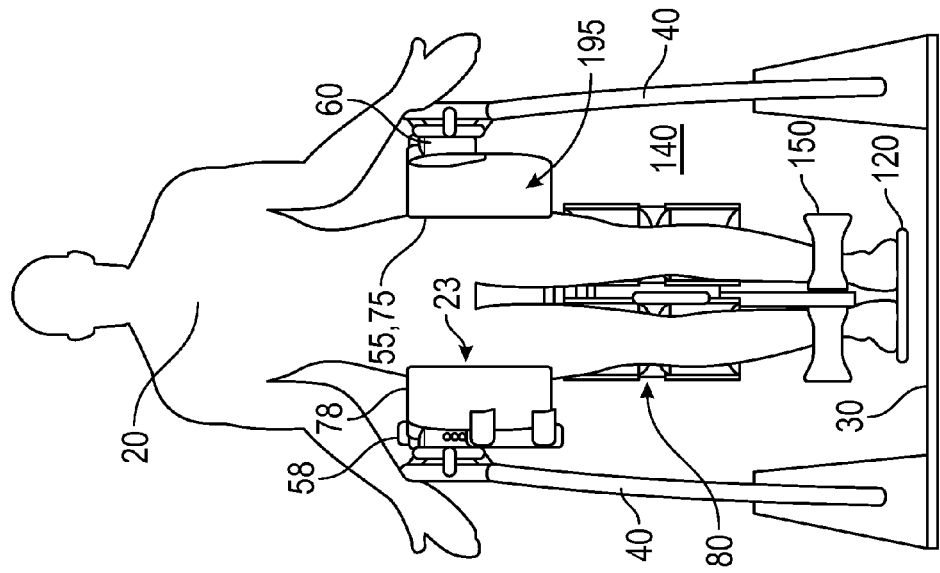
FIG. 3 is a front elevational view thereof.
Figure 2:
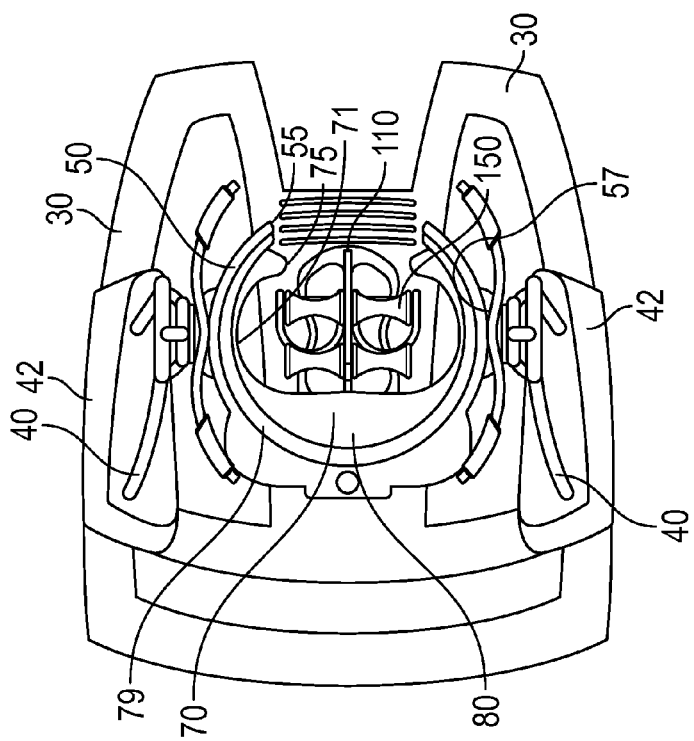
FIG. 2 is a top plan view thereof.

FIGS. 1-3 show an exercise device 10 for facilitating exercising of a person 20 on a floor surface 15. The floor surface 15 may also be a platform (not shown), or even a non-horizontal surface (not shown). The exercise device 10 includes a rigid base 30 for supporting the exercise device 10 on the floor surface 15. The base 30 may be bolted to the floor surface for additional stability, or may be made of a heavy material with a wide-enough footprint so as to be stable regardless of the position of the exercise device 10 and the person 20 therein.

At least one frame 40, and preferably two frames 40, are fixed with and extend upwardly from the base 30. Each frame 40 has a lower end 42 and an upper end 48, and is made with a strong, rigid material such as a metallic material.

An outer barrel 50 is rotationally fixed with the upper end 42 of each frame 40 at a tilt mechanism 60. The outer barrel 50 has an outer side 59, an inner side 51, and is open from a top side 58 to a bottom side 52 thereof for accommodating the person 20 therein. The outer barrel 50 has an opening 55 therethrough for allowing ingress and egress of the person 20 into the outer barrel 50. The outer barrel 50 may be multiple rigid parts (FIG. 10) adapted to surround and retain other components of the exercise device 10 as discussed below.

The tilt mechanism 60 preferably allows the person 20 to adjust the tilt of the outer barrel 50 with respect to vertical anywhere from 0 to 135 degrees or more, either forward or backward. The tilt mechanism 60, in a simple embodiment (not shown), includes a rotational bearing having a locking bolt (not shown) traversing therethrough to lock the position of the bearing when the locking bolt is engaged. The locking bolt may be disengaged by the person from within the outer barrel by manual actuation, such as by depressing a spring-biased button 220 on a first control handle 180 fixed with the frame 40 that allows the person 20 to position the outer barrel 50 at any angle with respect to the frame 40 and then lock that position in place by letting go of the spring-biased button 220 to engage the locking bolt. Alternately, the first control handle 180 may be mechanically coupled to a pressurized gas piston for at least partially assisting in the tilting of the outer barrel 50.

Figure 10:
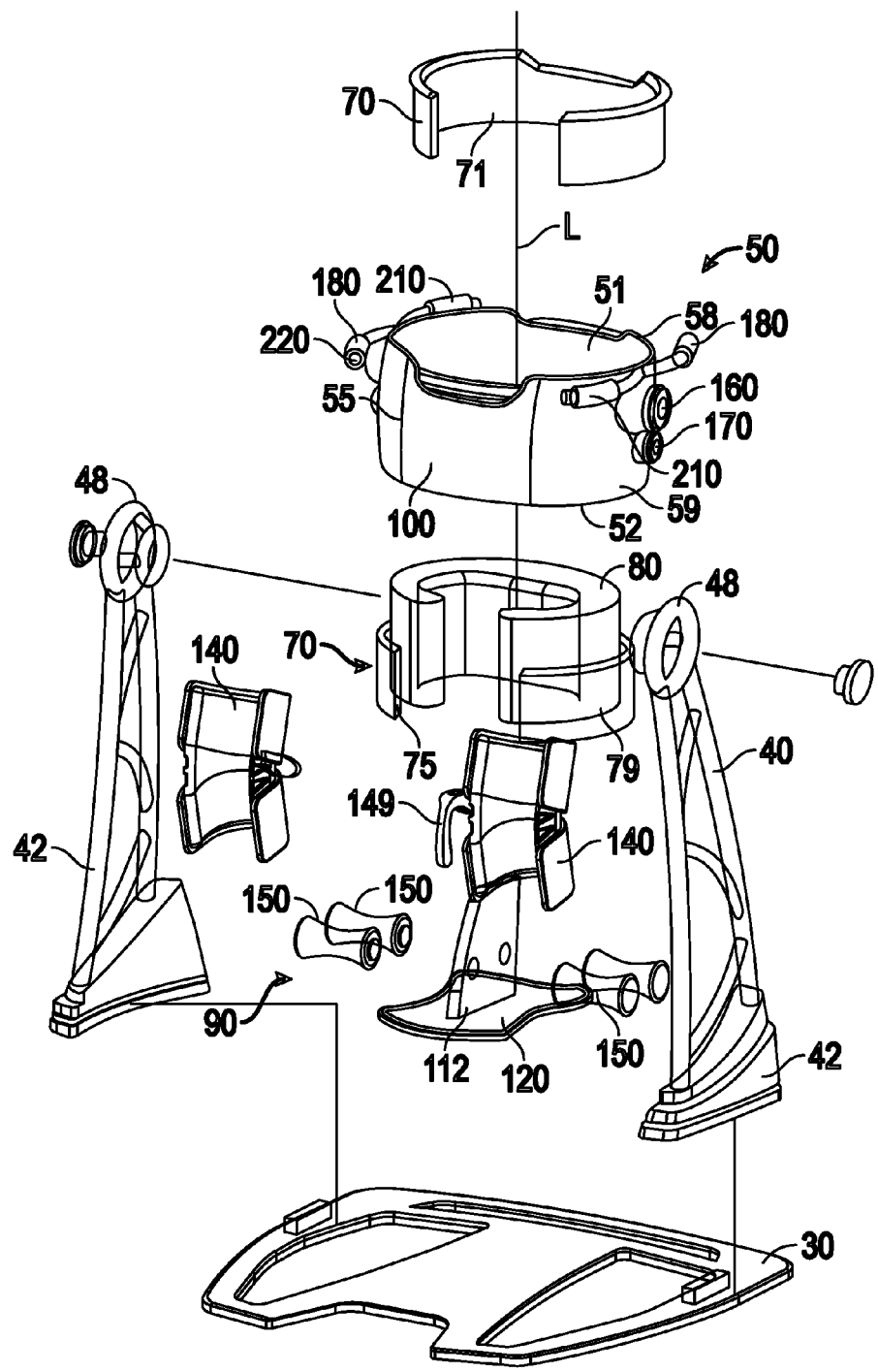
FIG. 10 is an exploded perspective view of one embodiment of the invention.
Figure 11:
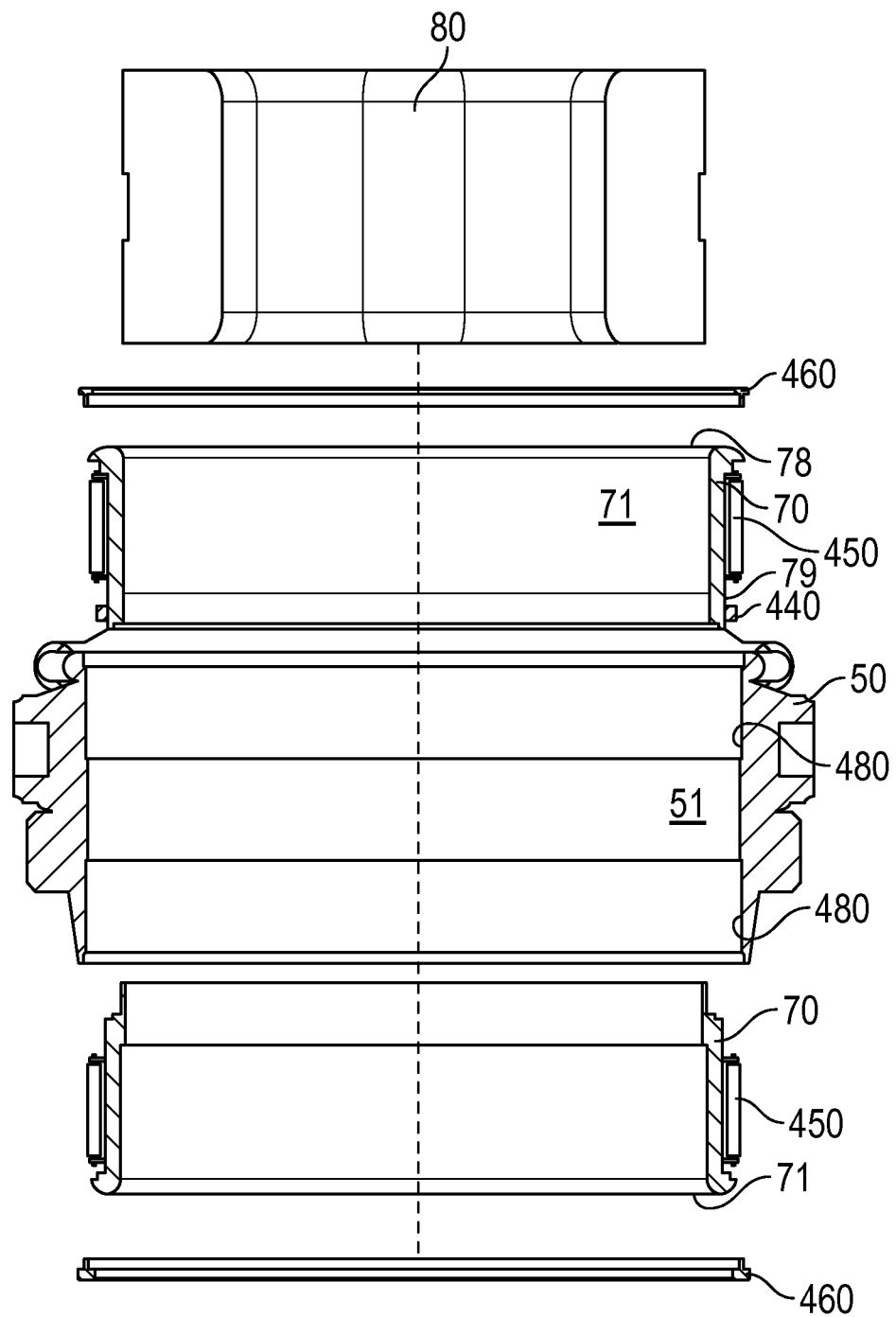
FIG. 11 is an exploded cross-sectional view of one embodiment of the inner barrel.

An inner barrel 70 has an outer side 79, an inner side 71, and is open from a top side 78 to a bottom side 72. The inner barrel 70 is rotationally fixed with the inner side 51 of the outer barrel 50 at a spin mechanism 190 and shares a common longitudinal axis L therewith through the top sides 58,78 and bottom sides 52,72 (FIG. 10). The inner barrel 70 includes an opening 75 therethrough for allowing ingress and egress of the person 20 into the inner barrel 70. The inner barrel 70 preferably includes an upper section and a lower section that fit together in such a way as to rotationally trap the inner barrel 70 within the outer barrel 50. A plurality of vertical rollers 450 (FIG. 11) ride within peripheral roller tracks 480 of the inner side 51 of the outer barrel 50. Retaining rings 460 prevent the upper and lower sections of the inner barrel 70 from separating from each other or from the outer barrel 50. Each section may include three, four or more of the vertical rollers 450 spaced evenly around the other side 79 of the inner barrel 50, and a circumferential gear cog ring 440 may be fixed therebetween as part of the spin mechanism 190.

The spin mechanism 190, in a simple embodiment (not shown), includes a rotational bearing surrounding the inner barrel 70 and having a locking bolt (not shown) traversing therethrough to lock the position of the bearing when the locking bolt is engaged. The locking bolt may be disengaged by the person from within the inner barrel 70 by manual actuation, such as by depressing a spring-biased button 220 on a second control handle 210 fixed with the frame 40 that allows the person 20 to position the inner barrel 70 at any angle with respect to the outer barrel 50 and then lock that position in place by letting go of the spring-biased button 220 to engage the locking bolt. Alternately, the second control handle 210 may be mechanically coupled to a pressurized gas piston for at least partially assisting in the rotating of the inner barrel 70.

In a preferred embodiment, the first control handle 180 and second control handle 210 are each pivotally fixed with the outer barrel 50 at a pair of ratchet mechanisms 181 (FIG. 13) that, with each pull of the handles 180,210, tilts the outer barrel 50 forward a predetermined angular amount and then locks that tilt position (FIGS. 14-16). Likewise, pushing the control handles 180,210 forward tilts the outer barrel 50 backward a predetermined angular amount and then locks that tilt position. The control handles 180,210 are each spring-biased into a neutral position in such an embodiment and tilt with the outer barrel 50. In embodiments wherein the person may enter the inner barrel 70 either facing forward or rearward (FIG. 5B), two opposing sets of the first and second control handles 180,210 may be included.

Figure 12:
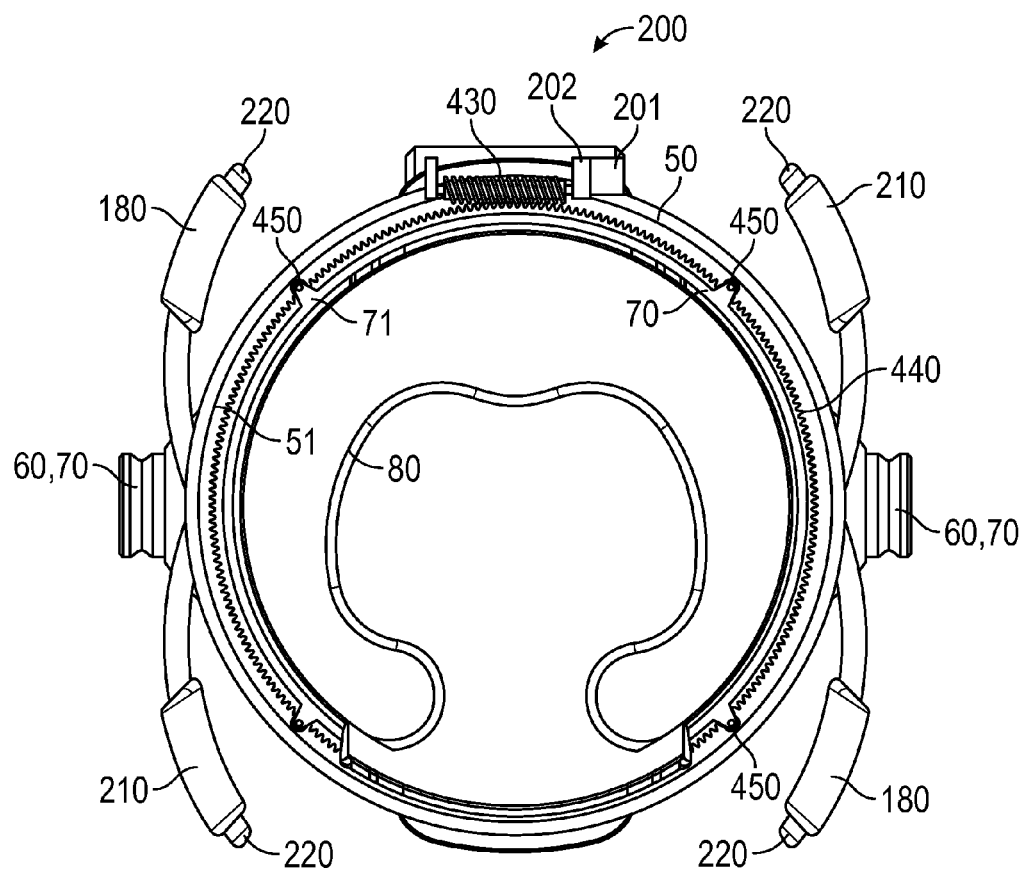
FIG. 12 is a top plan view of one embodiment of a spin mechanism of the inner and outer barrels.

Preferably in such an embodiment, the spring-loaded button 220 acts to disengage a worm gear 430 (FIG. 12) from a gear cog ring 440 of the inner barrel 70 to allow free manually-induced rotation thereof until the button 220 is released, whereby the worm gear 430 locks back into the gear cog ring 440 to lock the rotational position of the inner barrel 70 with respect to the outer barrel 50. All of the four buttons 220 on the two sets of first and second control handles 180,210 operate identically and in unison, and may be manually powered or electrically powered with solenoids (not shown) or the like.

At least one cushion 80 is fixed with the inner side 71 of the inner barrel 70 to support the person 20 therewithin. In one embodiment, each cushion 80 of the inner barrel 70 is adapted to fit the person's pelvis 23 in either a forward (FIG. 3) or backward (not shown) orientation. In one embodiment, at least one of the cushions 80 is inflatable to an extent capable of retaining the person within the inner barrel 70 even with the person 20 and the inner barrel 70 inverted.

A leg support mechanism 90 projects downwardly from the bottom side 72 of the inner barrel 70. The leg support mechanism 90 is adapted to support the person's feet 21 and legs 22 when the person 20 is positioned within the inner barrel 70, and may further include a leg support frame 110 fixed at a top end 118 thereof with the inner barrel 70. The bottom end 112 of the leg support frame 110 terminates at a foot platform 120 for supporting the person's feet 21 thereon.

Figure 7A:
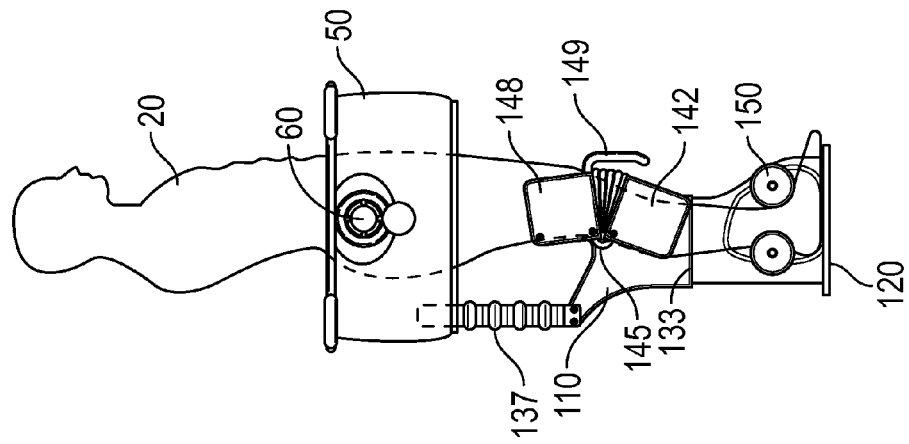
FIG. 7A is a side elevational view of the leg support mechanism set at a relatively short height, a stand and base omitted for clarity of illustration.
Figure 7B:
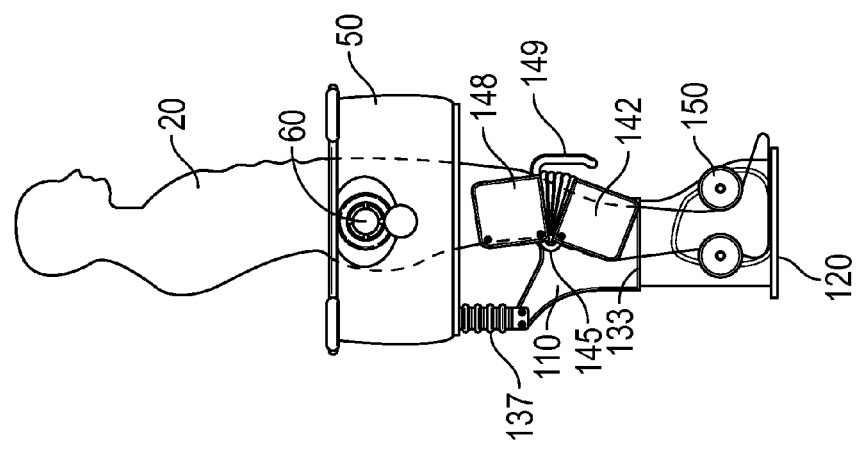
FIG. 7B is a side elevational view of the leg support mechanism set at a medium height, a stand and base omitted for clarity of illustration.
Figure 7C:
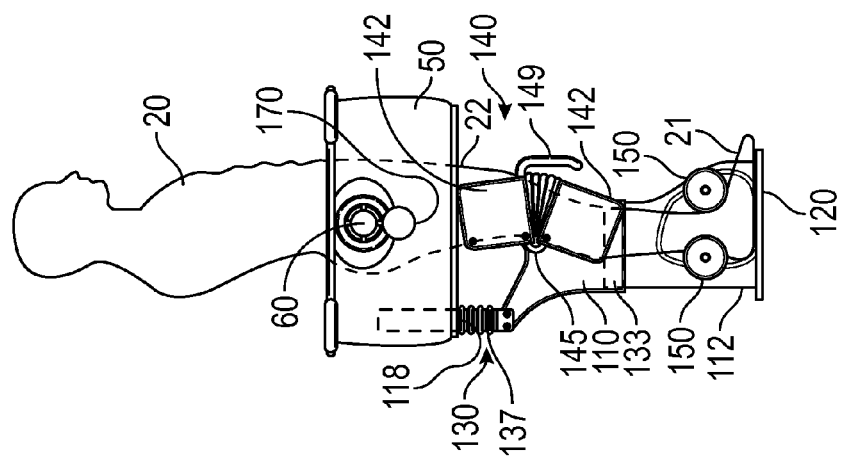
FIG. 7C is a side elevational view of the leg support mechanism set at a relatively tall height, a stand and base omitted for clarity of illustration.

Preferably the leg support frame 110 includes at least one height adjustment mechanism 130 to accommodate persons 20 with varying leg lengths (FIGS. 7A-7C). Preferably the leg support frame 90 includes both an upper adjustment mechanism 137 for adjusting the height of the leg support mechanism 90 between the person's pelvis 23 and his knees 25, and a lower adjustment mechanism 133 for adjusting the height of the leg support mechanism 90 between the person's knees 25 and his feet 21. Such height adjustment mechanisms 130,133,137 may be any of those found in the art that are able to retain their locked position when locked. Such height adjustment mechanism 130,133,137 may be pneumatically or hydraulically powered, may include linear actuators for electronically controlling the height adjustment, or may be manually set. Once set for a particular person 20, the height adjustment mechanism 130,133,137 are all locked in place so as not to change during the person's exercising.

Figure 4A:
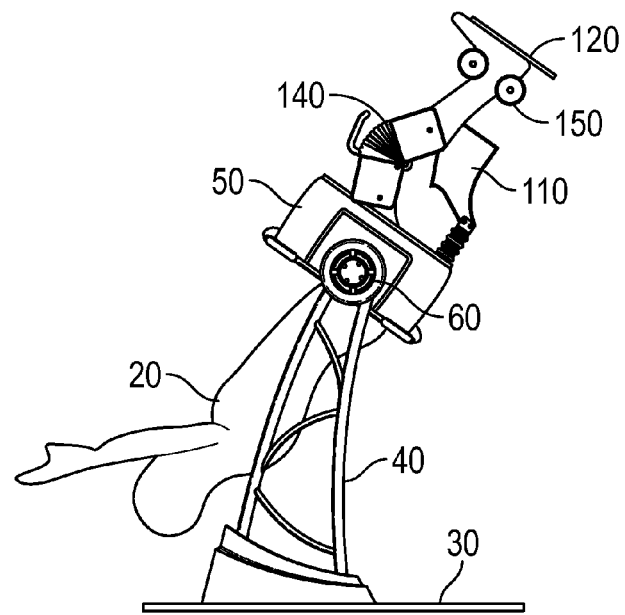
FIG. 4A is a side elevational view of the invention with the outer barrel set at an inclined angle.
Figure 4B:
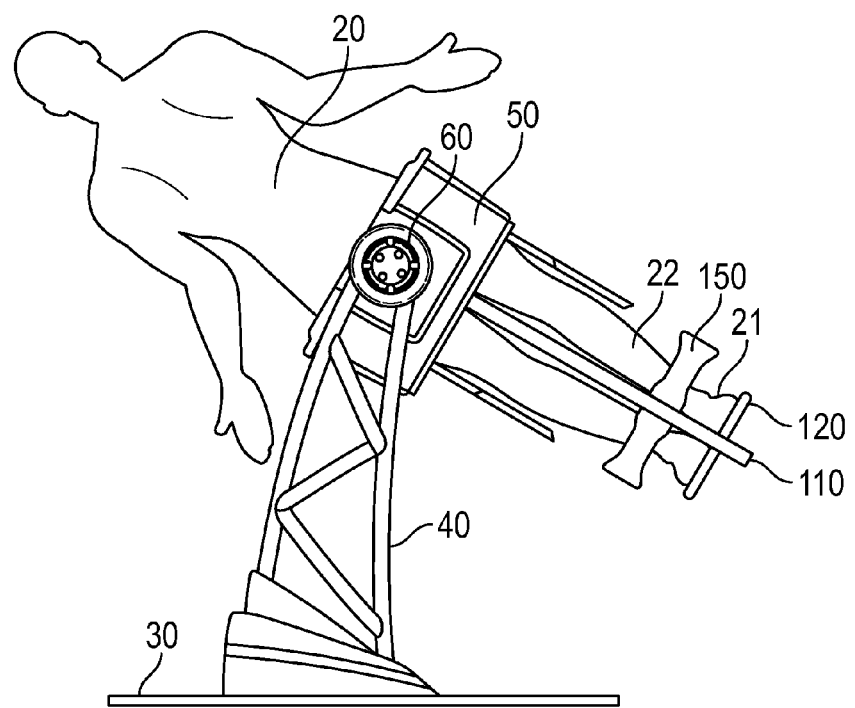
FIG. 4B is a side elevational view of the invention with the outer barrel set at an inclined angle and the inner barrel set at a 90-degree angle.
Figure 4C:
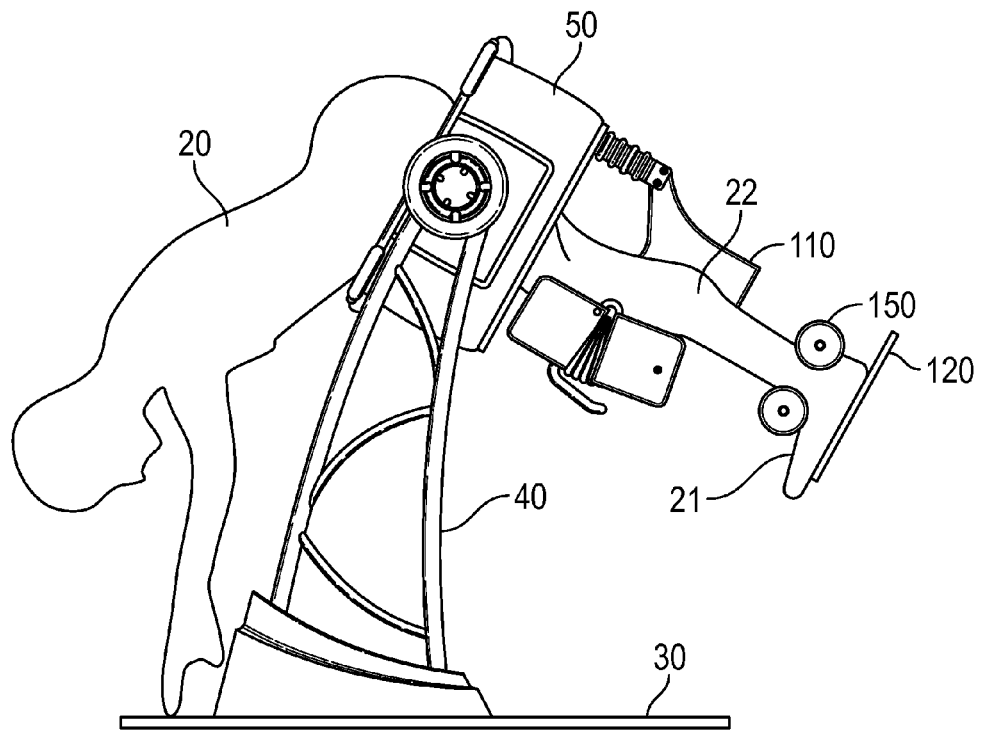
FIG. 4C is a side elevational view of the invention with the outer barrel set at an inclined angle and the inner barrel set at a 180-degree angle.

A pair of knee cuffs 140 may be included, each knee cuff 140 having an upper cuff 148 and a lower cuff 142 that are mutually pivotally attached at a back pivot 145 thereof. The back pivot 145 is lockable with a locking lever 149 to prevent mutual rotation between each cuff 148,142. The locking lever 149 may include a cam arrangement for binding the back pivot 145 into a fixed and locked position when the locking lever 149 is in a locked position. The leg support mechanism 110 may further include, for each of the person's feet 21, at least one, and preferably two, padded foot bolster 150 for aiding in supporting the person 20 in positions where the outer barrel 50 is tilted beyond 90-degrees in either direction (FIG. 4A).

In use, with the person 20 positioned within the inner barrel 70 and with his feet 21 and legs 22 supported by the leg support mechanism 90, the person 20 may be tilted with respect to vertical and rotated with respect to the axis of the barrels 50,70 in order to achieve different orientations in which to do exercises for exercising various muscles and muscle groups. Depending upon the selected tilt of the outer barrel 50 and the selected rotation of the inner barrel 70, such muscle groups may include, for example, the torso, core, mid-section, rectus abdominals, transversus abdominis, lower back, internal oblique, external oblique, latissimus dorsi, serratus anterior, serratus posterior inferior, erector spinae, external intercoastal, gluteus maximus, and gluteus medius muscle groups.

Figure 5A:
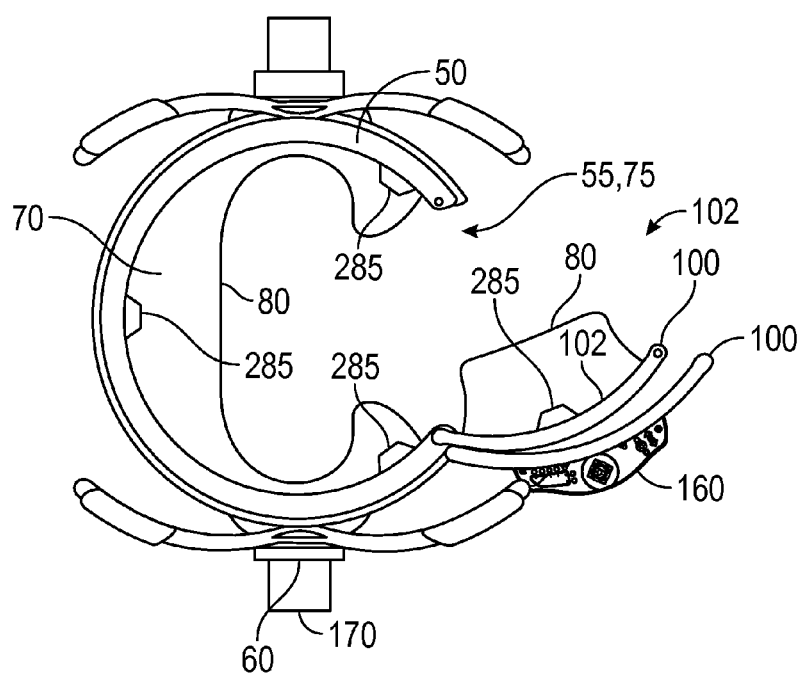
FIG. 5A is a partial top plan view of one embodiment of the invention, illustrating a door section of each barrel in an open position, and illustrated with a leg support mechanism and base omitted for clarity of illustration.
Figure 5B:
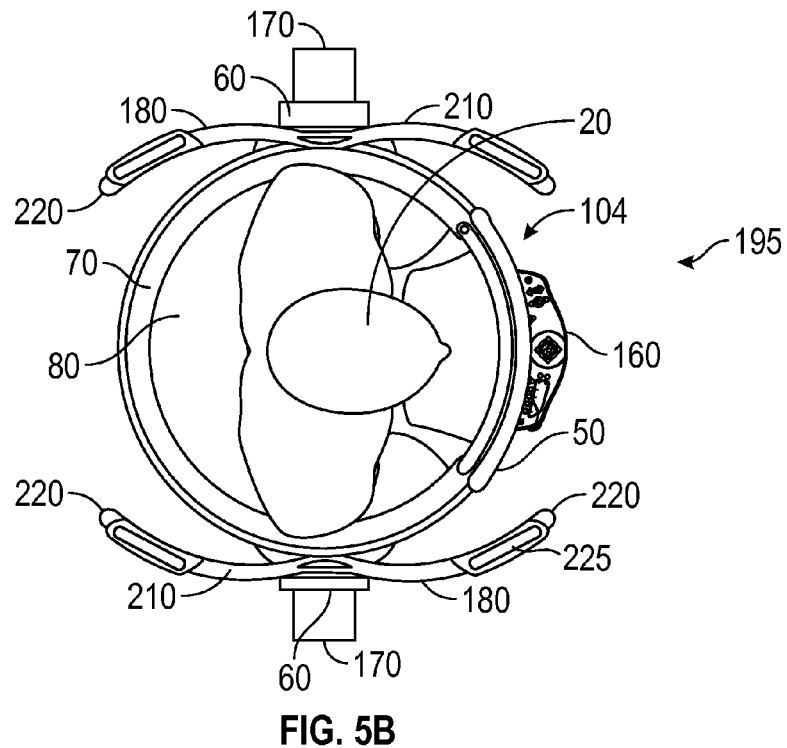
FIG. 5B is a top plan view of FIG. 5A but shown with the door sections in a closed position.
Figure 5C:
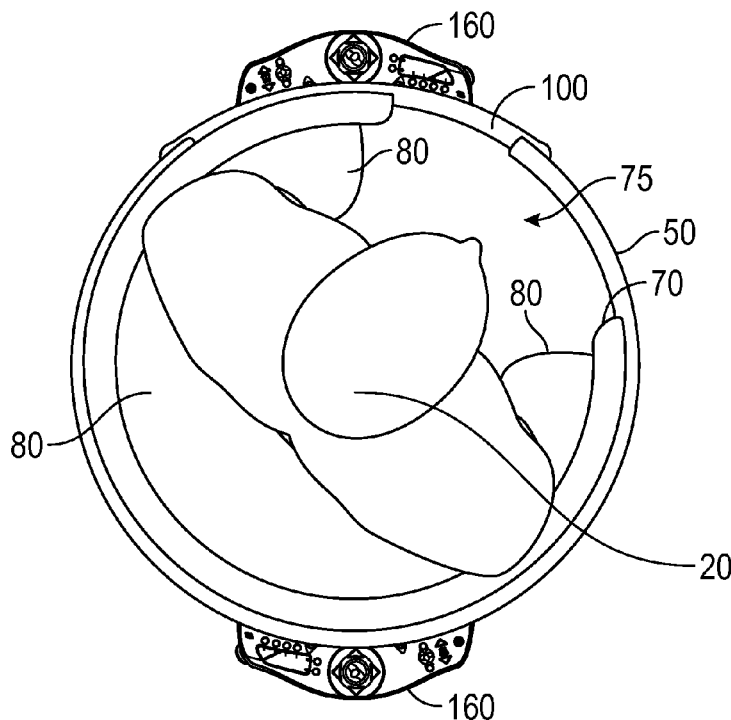
FIG. 5C is an enlarged top plan view of FIG. 5B, but shown with the inner barrel section rotated to a 45-degree angle and with the base and control handles omitted for clarity of illustration.

In at least one embodiment, each barrel 50,70 includes an at least partially removable or pivotable door section 100 at the opening 45,75 thereof (FIGS. 5A, 5B). Each door section 100 has at least one of the cushions 80 on an inner side 102 thereof and is moveable between an open position 102 to allow ingress and egress of the person 20 into and out of each barrel 50,70, and a closed position 104 wherein each door section 100 and the at least one cushion 80 cooperate with the at least one cushion 80 of the inner barrel 70 to securely hold the person's pelvis 23 within the inner barrel 70 between the cushions 80. Each door section 100 is able to be locked in place, either manually or electrically by a suitable locking mechanism (not shown), as is known in the art.

In at least one embodiment, the exercise device 10 further includes an electric control console 160, which is controllable by the person 20 when positioned within the inner barrel 50. Each tilt mechanism 60, in such embodiments, includes a powered drive mechanism 170 to tilt the outer barrel 50 with respect to the frame 40 in accordance to commands issued by the control console 160. The powered drive mechanism 170 may include at least one pneumatic or hydraulic cylinder 310 and at least one electrically-actuated valve 305, both controllable by the control console 160 to move the tilt mechanism 60 (FIGS. 9A and 9B) through a gear reduction arrangement 330.

In an alternate embodiment, the powered drive mechanism 170 includes an electric motor 320 and the gear reduction arrangement 330 (FIG. 18). Or, in yet another alternate embodiment, the electric motor 320 may drive another worm gear arrangement 430 that is engaged with a gear 431 that is fixed with the frame 40 (FIGS. 17A and 17B). Alternate types of powered drive mechanisms 170 may be employed to tilt the outer barrel 50 with respect to the frame 40, as is known in the art, provided that once a tilt position of the outer barrel 50 is set the barrel 50 is locked into place and immovable by the person 20 performing exercises, except that the tilt mechanism 170 may include a shock-absorbing mechanism (not shown) with pneumatic cylinders, springs or the like to absorb shock resulting from the exercising movements of the person 20.

Figure 8:
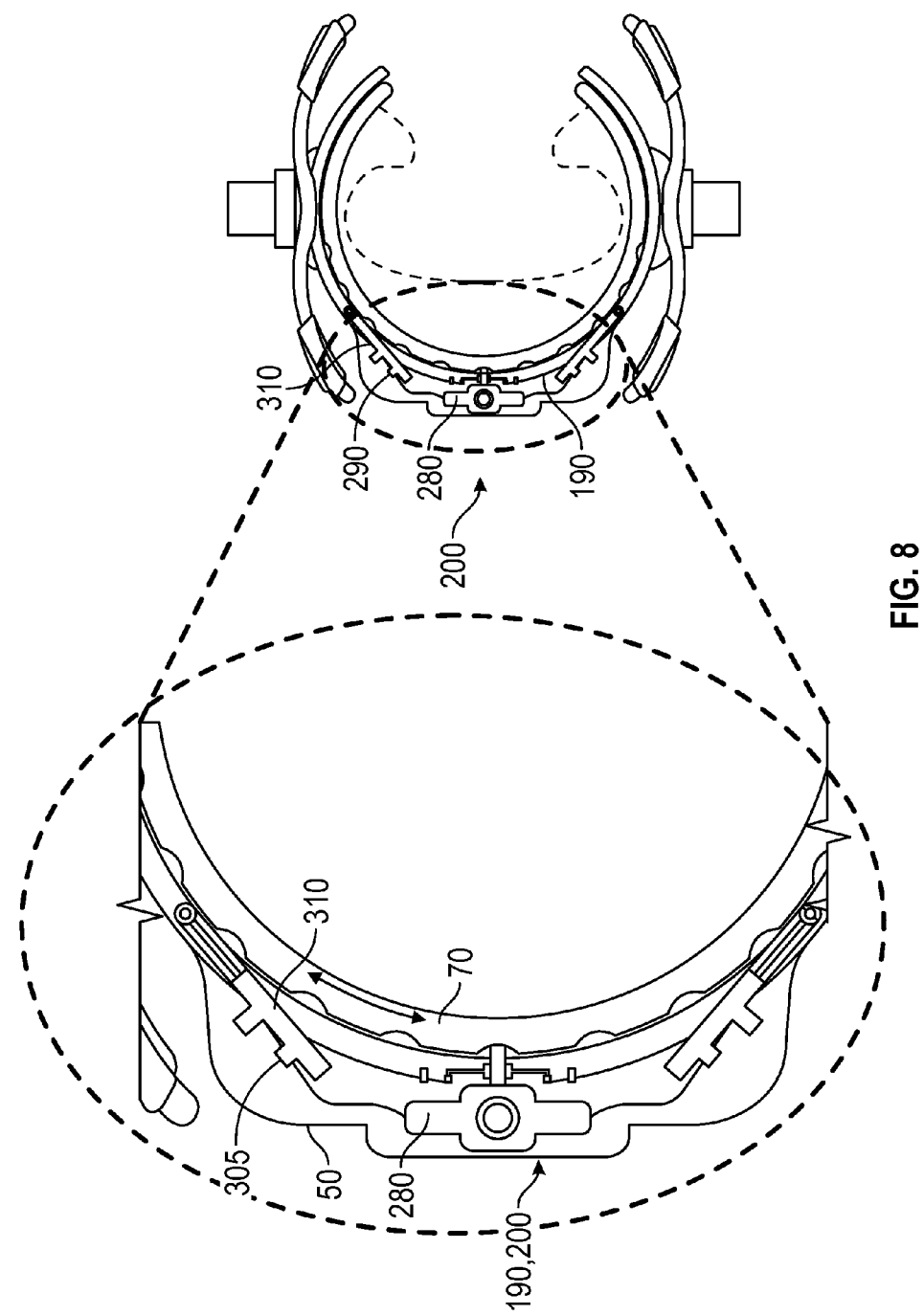
FIG. 8 is a diagram of one embodiment of a spin mechanism for rotating the inner barrel with respect to the outer barrel.
Figure 9A:
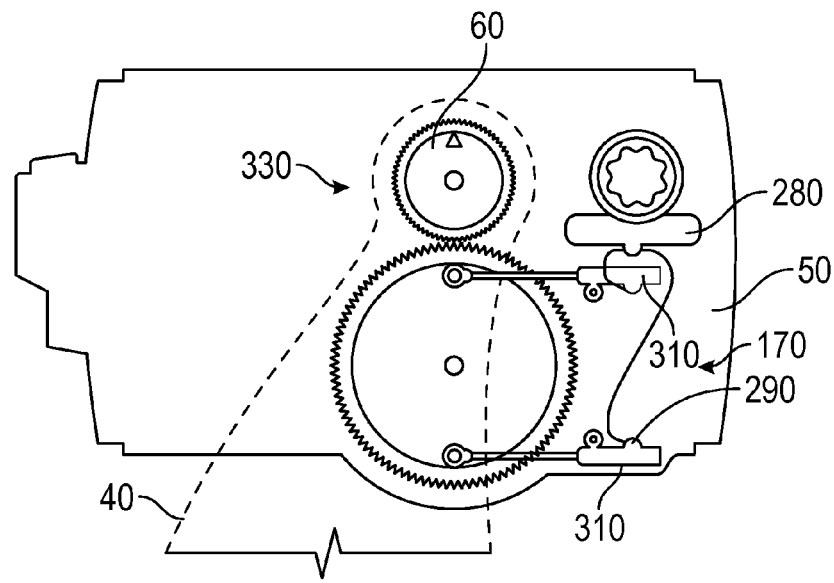
FIG. 9A is a diagram of two different embodiments of a tilt mechanism for tilting the outer barrel and inner barrel with respect to the frame and base, shown with the tilt set at a default position.
Figure 9B:
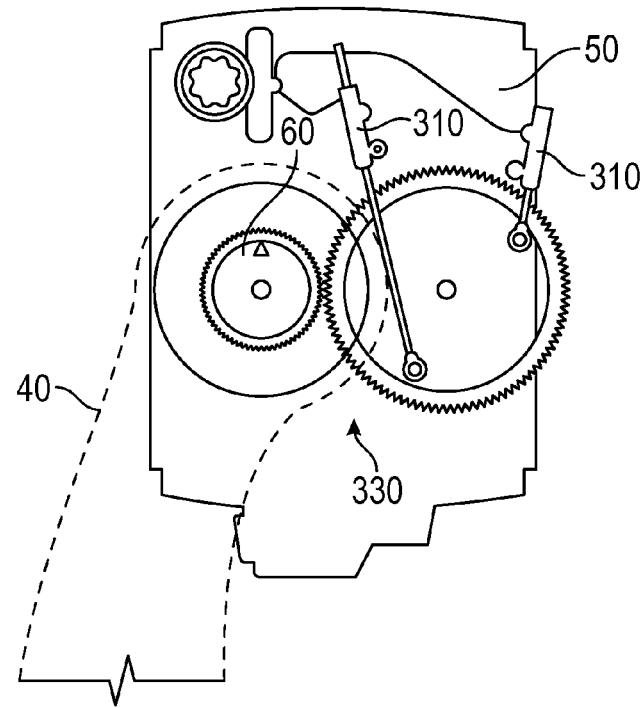
FIG. 9B is a diagram one of the embodiments of FIG. 9A, but showing the tilt set at 90-degrees.

A powered spin mechanism 190 may be further included and fixed between the inner and outer barrels 50,70, the spin mechanism 190 including a powered drive mechanism 200 to rotate the inner barrel 70 with respect to the outer barrel 50 in accordance to command issued by the control console 160. Each powered drive mechanism 170,200 may include at least one pneumatic or hydraulic cylinder 310 and at least one electrically-actuated valve 305, both controllable by the control console 160 to move the spin mechanism 190 (FIGS. 8, 9A, and 9B).

In an alternate embodiment (FIGS. 11 and 12), the powered drive mechanism 200 includes an electric motor 201, a gear reduction arrangement 202, a worm drive 430, and a gear cog ring 440 about a perimeter of the inner barrel 70 to move the inner barrel 70.

Any suitable powered drive mechanism 200 may be utilized, as is known or becomes known in the art, provided that once stopped the powered drive mechanism 200 locks or allows to be locked the inner barrel 70 with respect to the outer barrel 50.

To aid in emergency control of the embodiments that include the power drive mechanisms 170,200, the first and/or second control handles 180,210 may each include a conductor 225 electrically coupled with the control console 160 for detecting contact therewith by the person's hand. Alternately, or additionally, the button 220 on each control handle 180,210 is adapted to be an emergency stop button 220. As such, when contact is made between the person 20 and the conductor 225, or when the emergency stop button 220 is actuated, the control console 160 commands the tilt and spin mechanisms 60,190 to return to a default position 65,195, respectively (FIGS. 1 and 2). In such an embodiment, the first and second control handles 180,210 are fixed with either the outer barrel 50 (FIG. 5B) or the inner barrel 70 (not shown).

Preferably the control console 160 further includes at least a processor 230, a computer-readable storage medium 240, a display 250, an input interface 260, and a network interface 270. In one embodiment, multiple identical control consoles 160 are included and fixed with the outer barrel 50 (FIG. 5A) so that regardless of the orientation of the inner barrel 70 with respect to the outer barrel 50, the person 20 may reach and use one of the control consoles 160. Alternately, a single control console 160 may be fixed with the door section 100 of the inner barrel 70, so that the control console 160 is always directly in front of the person 20 using the device 10. The input interface 260 may include a plurality of dedicated-use buttons, so-called "soft buttons" that change function depending on what is indicated on the display 250, pointing interfaces such as touchpads or mouse-input type devices (not shown), or the like. In one embodiment, the display 250 includes a remote TV or monitor that is either wirelessly connected with the control console 160 through the network interface 270 or a wired interface (not shown).

In embodiments wherein the control console 160 or other electronic components are fixed with the inner barrel 50, a ribbon cable (not shown) or electrically-conductive brush arrangement (not shown) may be used to convey electric power and electric signals between the inner barrel 70 and the outer barrel 50. The inner barrel 70 is necessarily prevented from full 360 rotation with respect to the outer barrel 50 in embodiments having the ribbon cable. Other electrical components such as wires, relays, power cords, transformers, and the like are included as necessary to accomplish the goals of the invention, as known in the art. Preferably such other components are hidden from sight as much as possible during normal use by the base 30, frame 40, outer barrel 50, inner barrel 70 and cushions 80.

The computer-readable storage medium 240 may include, but not limited to, a hard disk, a flash memory, a CD, a DRAM or the like, an optional combination thereof, a server/database, etc. and may be used to cause the processor 230 to perform the steps of the methods disclosed herein. The computer-readable storage medium 240 may be a non-transitory computer-readable medium, and/or the computer-readable medium may comprise all computer-readable media, with the sole exception being a transitory, propagating signal. The computer-readable storage medium 240 may include media that store information for predetermined or limited or short period(s) of time and/or only in the presence of power, such as, but not limited to Random Access Memory (RAM), register memory, processor cache(s), etc.

In accordance with at least one aspect of the present invention, the methods, apparatuses employing electrical components, hardware, software, processors 230 for the software and computer-readable storage mediums 240 related to the processors 230 may be achieved utilizing suitable hardware, such as, but not limited to, that illustrated in the figures. Such hardware may be implemented utilizing any of the known technologies, such as standard digital circuitry, any of the known processors 230 that are operable to execute software and/or firmware programs, one or more programmable digital devices or systems, such as programmable read only memories (PROMs), programmable array logic devices (PALs), etc. Processors 230 may also include and/or be made of one or more microprocessors. Still further, the various aspects of the invention may be implemented by way of software and/or firmware program(s) that may be stored on suitable storage medium (e.g., computer-readable storage medium 240, hard drive, etc.) or media (such as floppy disk(s), memory chip(s), etc.) for transportability and/or distribution. The hardware, such as, but not limited to, a processor 230, computer-readable storage medium 230, hard drive, etc., may be located in the device 10, such as, but not limited to, in or near the one or more control panels or consoles 160, and/or may be located remotely from the machine or apparatus, such as in the portable electronic device 18 or the like.

With such a computer-controlled embodiment, the air pressure within each inflatable cushion 80 of the inner barrel 70 may be read by an air pressure sensor 285 and controlled by the control console 160, which can actuate an air pump 280 to inflate the cushion 80, or actuate an electrically-actuated pneumatic valve 290 to bleed-off air within the cushion 80 into the environment. The cushions 80 are deflated when the person 20 wishes to exit the exercise device 10 and when the barrels 50,70 are in their default positions 65,195, and inflated once the person 20 is positioned within the inner barrel 50 and indicates he is ready to start exercising. The person 20 may also manually adjust the inflation pressure of the cushions 80 for comfort and support as needed. In such an embodiment, with the air pump 280 off and the pneumatic valve 290 closed, the air pressure sensor 285 can detect movement of the user by registering changing air pressure within the cushions 80 related to pressure applied by the person 20 to the cushions 80.

Figure 6A:
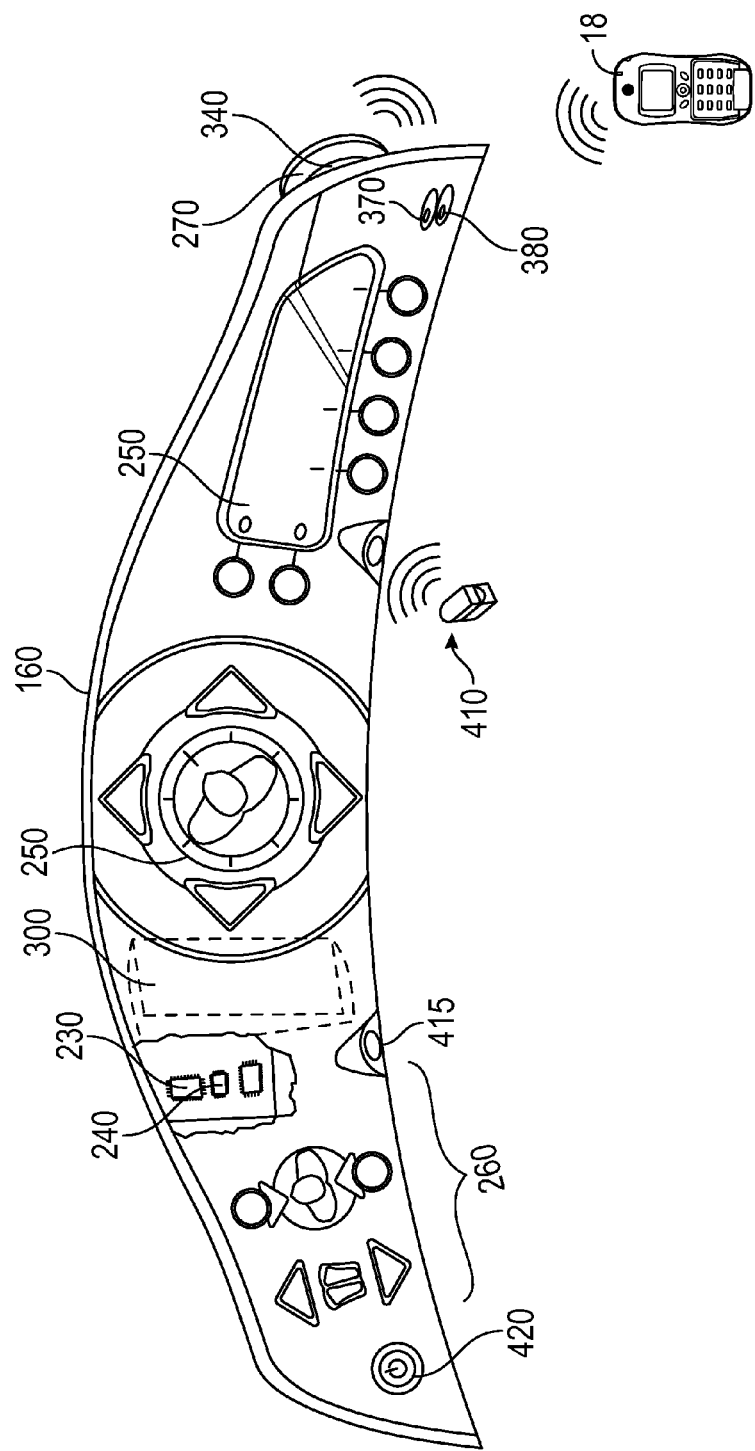
FIG. 6A is a diagram of a control console of one embodiment of the invention.

In such a computer-controlled embodiment, the control console 160 is programmed to return the tilt and spin mechanisms 60,190 to their default positions 65,195 if an emergency condition is detected, such as detecting no activity or movement of the person for a predetermined period of time based on monitoring fluctuations in air pressure in the cushions 80 or a separate motion sensor 415 (FIG. 6A), an electrical ground fault, a power failure, actuation of an emergency stop button 220, deactivation of the control console 160 by the person 20, or the like. In the case of a power failure or deactivation of the control console 160, the exercise device 10 further preferably includes a rechargeable battery 300 of sufficient capacity to return the tilt and spin mechanisms 60,190 to their default positions 65,195.

The network interface 270 is preferably a wireless network interface 340, wherein the control console 160 is programmed to receive commands from a remote electronic device 18 (FIG. 6A) of the person 20 or a training coach of the person 20, for example, such as a portable smart phone 18 running an exercise application thereon. The control console 160, in such an embodiment, provides exercise statistics of the person 20 to the remote electronic device 18 via the wireless network interface 340. Workout routines 350 may also be downloaded by the control console 160 via the wireless network interface 340.

Figure 6B:
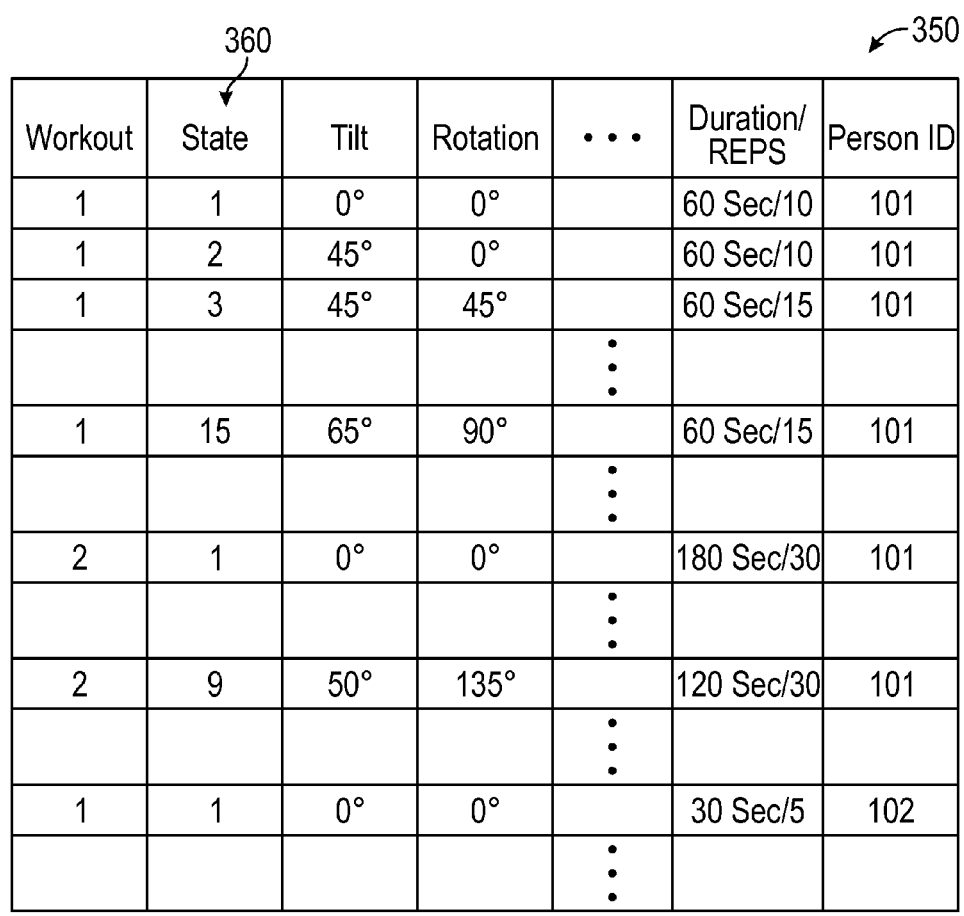
FIG. 6B is a chart representing a workout routine having different states of tilt and rotation of the barrels.

The processor 230 is adapted to follow instructions stored in the computer-readable storage medium 240 that enables the person 20 to store his desired workout routine 350 in the computer-readable storage medium 240. Pre-programmed workout routines 350 may be included with the exercise device 10, or customized workout routines 350 may be stored in the computer-readable storage medium 240 through use of the input interface 260 or the network interface 270 and a remote device. Such a customized workout routine 350 may be established by a health care professional or coach of the person 20, for example, through an internet-enabled remote device (not shown) in communication with either the portable electronic device 18 of the person 20 or the exercise device 10 directly. Such a workout routine 350 (FIG. 6B) includes one or more states 360 that each include at least the position of the tilt mechanism 60 and the spin mechanism 190, desired air pressure in each of the cushions 80, and a duration of time to perform exercises in that position and/or a number of reps that are to be performed while in that position.

Periodicity of air pressure variations within each cushion 80 as detected by the pressure sensor 285 allows the control console 160 to count the number of repetitions of an exercise that the person 20 has performed with the tilt and rotation mechanisms 60,190 in a set position, and in this way the control console 160 can determine based on a prescribed workout routine 350 when to advance the tilt and rotation mechanisms 60,190 a next state 360 for the person 20 to start a new exercise.

The control console 160 may further include a microphone 370 and a speaker 380. The processor 230 in such an embodiment is adapted to display workout routine 350 information and workout statistics on the display 250, and also to audibly announce the information through the speaker 380 with a text-to-speech algorithm, as is known in the art. The processor 230 is further adapted to interpret spoken commands of the person 20 with the microphone 370 and a speech recognition algorithm. Such a spoken command may be, for example, "START" for signifying that the person 20 is ready to start a selected workout routine 350, commanding the inflatable cushions 80 to inflate to their designated air pressures, and to advance the tilt and spin mechanisms 60,190 thereafter to their designated positions as determined in the first state 360 of the workout routine 350. Alternately, the spoken command "STOP" may be intended to return the outer barrel 50 and the inner barrel 70 to their default positions 65,195, or the spoken command "NEXT" may be used for advancing the workout routine 350 to the next state 360, etc.

The control console 160 may further include at least one physiological sensor taken from the group of physiological sensors 410 including, but not limited to, a heart rate monitor, a body temperature sensor, a blood pressure sensor, and an oxygen absorption sensor. Such a physiological sensor 410 may be attached to the person 20 and include the wireless network interface, include a wired interface (not shown), or may be fixed with one of the cushions 80, for example. As such, physiological conditions and exercise statistics may be monitored and recorded by the control console 160 and transmitted through the wireless network interface 270 to the portable electronic device 18 or another remote device (not shown), a social media or other website (not shown), or the like. In the event that the heart rate of the person 20 exceeds a predetermined threshold, for example, the control console 160 can take emergency action to return the person 20 to the default position and stop the workout routine 350. Likewise, if the person's heart rate exceeds a predetermined threshold, the control console 160 may be programmed to advance to the next state 360, signifying that the person 20 is sufficiently "warmed up" to continue the workout routine 350.

The application running on the portable smart phone 18 may act as the control console 160 in some embodiments, allowing the person 20 to select or edit a workout routine 350, indicate he is ready to start the workout routine 350, monitor and record the number of repetitions of exercises performed by the person 20 through monitoring the air pressure sensors 285 of the inflatable cushions 80, monitor and record physiological states of the person 20 through monitoring of the at least one physiological sensor 410, advance the exercise machine to the next state 360 in a running workout routine 350, pause the workout routine 350 in a current position, return to the default positions 65,195 of the barrels 50,70, increment the duration or number of repetitions required at each step in the workout routine 350 over time, transmit exercise statistics and physiological parameters of the person 20 to a remote server, notify third parties of compliance to a workout routine 350, re-run and save a previously performed workout routine 350, allow a new person 20 to begin exercising on the exercise machine 10, and the like.

The illustrated materials may be substituted for equivalent or better known to those skilled in the art. Also, the materials shown are for illustrative purposes for at least one embodiment of the present invention, and may not be required or employed in every embodiment of the machine or apparatus.

The outer barrel 50 may include an injection molded ABS Plastic multi part housing may be mounted to an inner cold rolled steel framework using tamper resistant stainless Steel socket-head-cap-screws. Twin ring gears at either pivot point may be driven by twin high torque geared-down electric motors on either side, contained in plastic housings (not all shown).

The inner barrel 70 may include a circular Steel ring shape captured with over molded ABS Plastic, circular rack gear around perimeter, driven by a high torque geared-down electric motor located in cylindrical housing at rear side of barrel (not all shown).

The inflatable cushions 80 may be a combination of self-skinned Microban®-treated vinyl outer membrane, over soft open cell, molded foam or similar materials. Preferably, within this foam structure is an air-tight inflatable area, controlled with a low pressure air pump system. Preferably, the inflation and/or deflation parts are all contained within the inner barrel 70 perimeter, and rotate with the inner barrel 70, and may be connected via a spring loaded wire harness (not shown).

The handles 180,210 may be a 1" rolled steel tubing with high-durometer rubber grips pinned to the outer side 59 of the outer barrel 50 proximate the tilt mechanism 60. The handles 180,210 may be removable for serviceability.

The base 30 may include a laser cut steel with vinyl overcoat for durability, or powder coated to color. Other embodiments of the base 30 may be made from any suitable material that includes structural attributes to provide the aforementioned horizontal and/or vertical stability for the device 10.

The leg support mechanism 90 may comprise a combination of aluminum to save on weight in certain areas and Laser-cut steel plates where more strength is required. The ankle bolsters 150, inner shin guards (not shown), and inside of the knee cuffs 140 may be high-density polyurethane foam. All open-cell foam areas may include Microban treatment, knee cuffs 140 that are molded ABS with high glass fill content for strength and durability with anti-pinch areas covered in rubber bellows, sliding bushings and rods use nylon impregnated bushings to reduce wear and no lubrication is needed (not all shown).

The leg support mechanism 90 may be driven up or down via a high torque, screw-drive motor (not shown) located up inside the inner barrel. The motor assembly may be held in place via grade 5 steel hardware and welded steel bracketry to the inner barrel steel chassis. All pinch-point, rack gears, and lubricated areas (not all shown) may be covered with soft, flexible, rubber bellows Ankle lock bolsters 150 may comprise cast folded high density polyurethane foam with factory treated Microban® additive, attached to 1 inch diameter steel tubing connected to the bottom end 112 of the leg support frame 110.

One or more methods of using one or more embodiments of the exercise device 10 are as follows:

A person 20 opens one or both door sections 100 and walks into the barrels 50,70 standing either facing towards the back of the exercise device 10 or the person 20 turns around the faces towards the front of the exercise device 10 while standing on the foot platform 120. The person 20 may adjust the knee cuffs 140 either manually or electronically (or a combination of both) through the control console 160 to the desired position, or may manually adjust same without any electronic component in at least one embodiment. Once that position is correct, the person 20 may then close the door sections 100 which preferably lock into place. A power button 420 flashes, prompting the person 20 to press it to start a process of setting up and commencing a workout routine 350.

After the person 20 has turned on the power, the exercise device 10 prompts the person 20 by voice as well as with text in the display 250 that the person 20 needs to adjust his/her height setting. This is accomplished by the person 20 pressing a control on the input interface 260 to raise or lower the foot platform 120 to correctly adjust the proper placement of the person's hips, pelvis 23, and buttock in relation to being in the center to upper portion of the top side 78 of the inner barrel 70. Once the person 20 has the proper adjustment for his/her hips, pelvis 23, buttock, the person 20 then may inflate the cushions 80 through the console's input interface 260. When that is completed and the person 20 feels securely retained within the inner barrel 70, the voice and text prompts ask the person 20 to choose manual input for entering a workout routine 350 or to choose a prewritten workout routine 350. Once the person 20 chooses manual or prewritten workout routine 350 the voice and text prompt ask the person 20 a next question:

For example, the prompt may ask, "What muscle group do you want to exercise?" The touch screen then displays several choices, such as 1. Abdominal, 2. Oblique, or 3. Lower back. The person 20 touches a desired exercise on the display 250 or input interface 260 and then the person 20 is prompted to the next step or question.

For example, the prompt may then ask, "How many repetitions per isolated movement do you want to perform? (Ex 1-100)." The person 20 then enters a number of desired repetitions per isolated angle and then presses an "enter" button. Alternately, the person 20 speaks the desired number.

The touch screen display 250 then prompts the person 20 for the next step, for example, to set the tilt from 0 to 135 degrees (or any other predetermined range of degrees as discussed herein). Preferably, as the person 20 enters or changes the desired tilt angle, a tilt/rotation visual indicator (not shown) on the display 250 shows a representation of the entered angle so that the person 20 visually knows what the expected starting position will look like before the person 20 executes and initiates the program. Once that information is entered, the person 20 then chooses the number of degrees of rotation of the inner barrel 70 with respect to the outer barrel 50 in single or multiple degree increments. Based on standing in the exercise device 10 facing forward the degrees of rotation may be, in at least in one embodiment, equal to 90 degrees or further clockwise and 90 degrees or further counter clockwise. The same may hold true if the person 20 enters the exercise device 10 and faces backwards. The degree of rotation is 90 degrees clockwise and 90 counterclockwise in at least one embodiment. Based on this, the person 20 may achieve a full 360 degree workout, of his/her core muscles or mid-section with 100% complete rotation capability. A tilt/rotation representation on the display 250 provides the person 20 a preview of what he may expect.

Once the person 20 has completed these steps, the person 20 is almost ready for the workout to begin. The last choice is either to do this selected state 360 as a stand-alone workout routine 350, or to continue adding additional device states 360, each with different tilt and rotation settings. Once all of the desired states 360 are programmed into the storage medium 240, the person 20 then presses a flashing or illuminated start exercise program button, or speaks a voice command, whereupon the person 20 then gets a visual and/or voice countdown, for example, starting at "Five, Four, Three, Two, One, Go." Then the exercise device 10 goes into the first programmed state 360.

Example of an Abdominal Workout:

The exercise device 10 moves to a 135 degree tilt (FIG. 4A) and the person 20 does five crunch repetitions, the proximity sensor 415 detects each repetition and counts out loud via the speaker 380, and optionally displaying a simulated image of the person 20 onto the display 250.

Once the person 20 has completed the last of the five crunches the exercise device 10 automatically adjusts the rotation and tilt to the next device state 360 and holds it in place there until the person 20 has completed the next five repetitions, and so on until the all states 360 are completed.

Example of a Six Sequence Abdominal Workout Routine:

The exercise device 10 may be set for five repetitions per state 360, starting at 135 degree angle of tilt and zero degree angle of rotation. The person 20 performs the first sequence—five repetitions of straight up crunches. Once the exercise device 10 detects the last repetition, the inner barrel 50 rotates clockwise 15 degrees and holds it there for the beginning of the second state 360. After the person 20 has completed the last repetition in that sequence, the inner barrel 50 rotates clockwise to the 30 degrees location and holds the inner barrel 50 in place for the person 20 to begin the third sequence. After the person 20 completes the third sequence of 5 repetitions at that angle, the exercise device 10 detects the last repetition and moves the inner barrel 50 back past 0 degrees to 15 degrees counterclockwise and stops and holds at the fourth sequence until five repetitions are completed. The exercise device 10 then moves to the fifth state 360 which might be 30 degrees counterclockwise. Once the person 20 has completed the last repetition of the fifth state 360, the person 20 is moved into the last and final sixth state position, which is 0 degree of rotation and the outer barrel moves from the 135 degree of tilt to 90 degree of tilt and holds the barrels 50,70 in place. The person 20 performs their last five repetitions, and the exercise device 10 then automatically defaults back to the starting position 65,195 and releases the inflatable cushions 80 and unlocks the door sections 100, whereupon the person 20 may then exit the exercise device 10. The person 20 may program as many angle and tilt states 360 as desired within a single workout routine 350.

At any time, if the person 20 feels the need to pause his/her workout, the person 20 may grasp any of the support handles 180,210. If the person 20 desires to prematurely stop or abort the workout routine 350, any of the emergency stop buttons 220 may be depressed, or the voice command "STOP" issued. The emergency stop buttons 220 cause a momentary electrical stoppage and fail safe relays open, causing the exercise device 10 to assume a predetermined, defaulted starting position 65,195, and to deflate the cushions 80, and to unlock the door sections 100.

One or more embodiments of the exercise device 10 may include the ability to import multiple preprogrammed workout routines 350 that may be entered into the storage medium 240 via the input interface 260 or the networking interface 270. Additionally or alternatively, one or more embodiments of the exercise device 10 may have adjustable bolsters 150, which operate to move manually or automatically through the control console 160 and a linear actuator (not shown) or the like. Additionally, while the provided figures show the knee cuffs 140 as being adjusted manually, the adjustment of the knee cuffs 140 may be motorized and controlled through the control console 160.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necesary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An exercise device for facilitating exercising of a person on a floor surface, the exercise device comprising:
 a base for supporting the exercise device on the floor surface;
 at least one frame fixed with and extending upwardly from the base, each frame having a lower end and an upper end;
 an outer barrel rotationally fixed with the upper end of each frame at a tilt mechanism, the outer barrel having an outer side, an inner side, and open from a top side to a bottom side, the outer barrel having an opening therethrough for allowing ingress and egress of the person into the outer barrel;

an inner barrel having an outer side, an inner side, and open from a top side to a bottom side, the inner barrel rotationally captured with the inner side of the outer barrel and sharing a common longitudinal axis through the top and bottom sides with the outer barrel, the inner barrel having an opening therethrough for allowing ingress and egress of the person into the inner barrel, at least one cushion fixed with the inner side of the inner barrel to support the person within the inner barrel;

a leg support mechanism projecting downwardly from the bottom side of the inner barrel and adapted to support the person's feet and legs when the person is positioned within the inner barrel;

wherein the leg support mechanism further includes a leg support frame fixed at a top end thereof with the inner barrel and at a bottom end thereof with a foot platform for supporting the person's feet thereon, the leg support frame having a height adjustment mechanism to accommodate people with varying leg lengths; and wherein the leg support frame further includes a pair of knee cuffs, each knee cuff having an upper cuff and a lower cuff mutually pivotal at a back pivot thereof, the back pivot manually lockable with a locking lever to prevent mutual rotation between each upper and lower cuff whereby the person, when positioned within the inner barrel and with his feet and legs supported by the leg support mechanism, may be tilted with respect to vertical and rotated with respect to the longitudinal axis of the barrels in order to achieve different orientations in which to do exercises for exercising various muscles.

2. The exercise device of claim 1 wherein the at least one cushion of the inner barrel is adapted to fit the person's pelvis in either a forward or backward orientation.

3. The exercise device of claim 1 wherein at least one of the at least one cushion of the inner barrel is inflatable.

4. The exercise device of claim 1 wherein the inner and outer barrels each include an at least partially removable door section at the opening therethrough, the door section of the inner barrel having another of the cushions on an inner side thereof and being moveable between an open position to allow ingress and egress of the person from the inner barrel, and a closed position wherein the door section, inner barrel, and the cushions cooperate to securely hold the person's pelvis within the inner barrel between the cushions.

5. The exercise device of claim 1 wherein the leg support frame includes an upper adjustment mechanism for adjusting the height of the leg support mechanism between the person's pelvis and his knees, and a lower adjustment mechanism for adjusting the height of the leg support mechanism between the person's knees and his feet.

6. The exercise device of claim 1 wherein the leg support mechanism further includes at least one foot bolster to support the person's feet and ankles when substantially inverted.

7. The exercise device of claim 1 further including a first and second control handles fixed proximate the top side of the outer barrel, each control handle adapted for grasping by the person to allow manually tilting of the outer barrel with respect to the at least one frame and manually rotating of the inner barrel with respect to the outer barrel.

8. An exercise device for facilitating exercising of a person on a floor surface, the exercise device comprising:

a base for supporting the exercise device on the floor surface;

at least one frame fixed with and extending upwardly from the base, each frame having a lower end and an upper end;

an outer barrel rotationally fixed with the upper end of each frame at a tilt mechanism, the outer barrel having an outer side, an inner side, and open from a top side to a bottom side, the outer barrel having an opening therethrough for allowing ingress and egress of the person into the outer barrel;

an inner barrel having an outer side, an inner side, and open from a top side to a bottom side, the inner barrel rotationally captured with the inner side of the outer barrel and sharing a common longitudinal axis through the top and bottom sides with the outer barrel, the inner barrel having an opening therethrough for allowing ingress and egress of the person into the inner barrel, at least one cushion fixed with the inner side of the inner barrel to support the person within the inner barrel;

a leg support mechanism projecting downwardly from the bottom side of the inner barrel and adapted to support the person's feet and legs when the person is positioned within the inner barrel;

an electric control console controllable by the person when positioned within the inner barrel and wherein each tilt mechanism includes a powered drive mechanism to tilt the outer barrel with respect to the frame in accordance to commands issued by the control console; and a first and second control handles fixed proximate the top side of the outer barrel, each control handle including a conductor in electrical communication with the control console for detecting contact by the person's hand for signaling an emergency condition, causing the control console to command the tilt mechanism to a default position;

whereby the person, when positioned within the inner barrel and with his feet and legs supported by the leg support mechanism, may be tilted with respect to vertical and rotated with respect to the longitudinal axis of the barrels in order to achieve different orientations in which to do exercises for exercising various muscles.

9. The exercise device of claim 8 wherein the first and/or second control handle further includes an emergency stop button that, when actuated, causes the control panel to command the tilt mechanism to the default position.

10. An exercise device for facilitating exercising of a person on a floor surface, the exercise device comprising:

a base for supporting the exercise device on the floor surface;

at least one frame fixed with and extending upwardly from the base, each frame having a lower end and an upper end;

an outer barrel rotationally fixed with the upper end of each frame at a tilt mechanism, the outer barrel having an outer side, an inner side, and open from a top side to a bottom side, the outer barrel having an opening therethrough for allowing ingress and egress of the person into the outer barrel;

an inner barrel having an outer side, an inner side, and open from a top side to a bottom side, the inner barrel rotationally captured with the inner side of the outer barrel and sharing a common longitudinal axis through the top and bottom sides with the outer barrel, the inner barrel having an opening therethrough for allowing ingress and egress of the person into the inner barrel, at least one cushion fixed with the inner side of the inner barrel to support the person within the inner barrel;

a leg support mechanism projecting downwardly from the bottom side of the inner barrel and adapted to support the person's feet and legs when the person is positioned within the inner barrel;

an electric control console controllable by the person when positioned within the inner barrel and wherein each tilt mechanism includes a powered drive mechanism to tilt the outer barrel with respect to the frame in accordance to commands issued by the control console;

a spin mechanism fixed between the inner and outer barrels, the spin mechanism including a powered drive mechanism to rotate the inner barrel with respect to the outer barrel in accordance to commands issued by the control console; and the control console further includes at least a processor, a computer-readable storage medium, a display, an input interface, and a network interface;

wherein at least one of the at least one cushions of the inner barrel is an inflatable cushion, the air pressure therewithin controlled by the control console, an air pump, and at least one electrically-actuated valve;

whereby the person, when positioned within the inner barrel and with his feet and legs supported by the leg support mechanism, may be tilted with respect to vertical and rotated with respect to the longitudinal axis of the barrels in order to achieve different orientations in which to do exercises for exercising various muscles.

11. The exercise device of claim 10 further including at least one air pressure sensor within the at least one of the inflatable cushions, the control console adapted to determine the position and activity level of the person based on data from each air pressure sensor, a tilt position of the barrels, and a rotational position of the inner barrel.

12. The exercise device of claim 11 wherein the control console is adapted to return the tilt and spin mechanisms to their default positions if an emergency condition is detected, the emergency condition including: no user activity detected by the pressure sensors for a predetermined period of time, an electrical ground fault, or a power failure; the control console including a rechargeable battery or capacitor sufficient to return the tilt and spin mechanisms to the default positions in the event of a power failure.

13. The exercise device of claim 11 wherein each powered drive mechanism includes at least one pneumatic cylinder and at least one electrically-actuated valve controllable by the control console.

14. The exercise device of claim 11 wherein each powered drive mechanism includes an electric motor and a gear reduction arrangement.

15. The exercise device of claim 11 wherein the network interface is a wireless network interface, and wherein the control console is programmed to receive commands from a remote electronic device and to provide exercise statistics of the person to the remote electronic device via the wireless network interface.

16. The exercise device of claim 11 wherein the processor is adapted to follow instructions stored in the computer-readable storage medium that enables the person to store a workout routine that includes one or more states that include at least the position of the tilt mechanism and the spin mechanism, air pressure in each of the at least one cushion, and a duration, and further enables the person to replay the workout routine at a later time on the exercise device.

17. The exercise device of claim 10 wherein the control console further includes a microphone and a speaker, the processor being adapted to display information on the display and also to audibly announce the information through the speaker with a text-to-speech algorithm, the processor further adapted to interpret spoken commands of the person with the microphone and a speech recognition algorithm.

18. The exercise device of claim 10 wherein the computer readable memory includes a plurality of pre-programmed workout routines, each selectable by the person, each workout routine including one or more states that include at least the position of the tilt mechanism and the spin mechanism, air pressure in each of the at least one inflatable cushion, and a duration.

19. The exercise device of claim 10 wherein the processor of the control console is adapted to receive through the network interface one or more workout routines that each includes one or more states that at least include the position of the tilt mechanism and the spin mechanism, air pressure in each of the at least one inflatable cushion, and a duration.

20. The exercise device of claim 10 wherein the control console further includes at least one physiological sensor selected from the group of physiological sensors consisting of: a heart rate monitor, a body temperature sensor, a blood pressure sensor, and an oxygen absorption sensor.

21. The exercise device of claim 20 wherein the at least one physiological sensor is fixed with one of the cushions.

* * * * *